United States Patent
Debruyne

(10) Patent No.: US 11,771,705 B2
(45) Date of Patent: Oct. 3, 2023

(54) ADJUVANT THERAPY FOR USE IN PROSTATE CANCER TREATMENT

(71) Applicant: Fund SA, Liège (BE)

(72) Inventor: F. M. J. Debruyne, Arnhem (NL)

(73) Assignee: FUND SA, Liege (BE)

( * ) Notice: Subject to any disclaimer, the term of this patent is extended or adjusted under 35 U.S.C. 154(b) by 163 days.

(21) Appl. No.: 16/777,600

(22) Filed: Jan. 30, 2020

(65) Prior Publication Data
US 2020/0246354 A1 Aug. 6, 2020

Related U.S. Application Data

(63) Continuation of application No. PCT/EP2018/054470, filed on Feb. 23, 2018.

(30) Foreign Application Priority Data

Aug. 1, 2017 (EP) .................... 17184320

(51) Int. Cl.
*A61K 31/565* (2006.01)
*A61K 45/06* (2006.01)
*A61P 35/00* (2006.01)

(52) U.S. Cl.
CPC ............ *A61K 31/565* (2013.01); *A61P 35/00* (2018.01); *A61K 45/06* (2013.01)

(58) Field of Classification Search
CPC ........ A61K 31/565; A61K 45/06; A61P 35/00
See application file for complete search history.

(56) References Cited

U.S. PATENT DOCUMENTS

| | | | |
|---|---|---|---|
| 9,561,238 B2 * | 2/2017 | Coelingh Bennink | A61P 35/00 |
| 2007/0042040 A1 * | 2/2007 | Porchet | A61K 31/56 424/468 |

FOREIGN PATENT DOCUMENTS

| | | |
|---|---|---|
| WO | WO-94/26207 A1 | 11/1994 |
| WO | WO-2004/096259 | 11/2004 |
| WO | WO-2005/063276 | 7/2005 |

OTHER PUBLICATIONS

Spitz et al, Research and Reports in Urology (Aug. 23, 2016), vol. 8, pp. 159-164. (Year: 2016).*
Dutman et al, published abstract from presentation at ENDO 2017: The 99th Annual Meeting & Expo, Apr. 1-4, 2017. (Year: 2017).*
Dutman et al., "The effects of the human fetal estrogen estetrol (E4) in healthy men to estimate its potential use for the treatment of prostate cancer," European Urology Supplements, vol. 16, No. 3, (pp. e362-e364) Mar. 1, 2017, 3 pages.
Freedland et al., "Androgen deprivation therapy and estrogen deficiency induced adverse effects in the treatment of prostate cancer," Prostate Cancer and Prostatic Diseases 12 (pp. 333-338) 2009, 6 pages.

(Continued)

*Primary Examiner* — Craig D Ricci
*Assistant Examiner* — Janet L Coppins
(74) *Attorney, Agent, or Firm* — FOLEY & LARDNER LLP

(57) ABSTRACT

The present invention relates to the field of prostate cancer treatment, and in particular the field of prostate cancer treatment by Androgen Deprivation Therapy (ADT). The present treatment involves oral administration of an estetrol component in conjunction with ADT.

5 Claims, 15 Drawing Sheets

(56) References Cited

OTHER PUBLICATIONS

Hammond et al., "Esterol does not bind sex hormone binding globulin or increase its production by human HepG2 cells," Climacteric 11, Supplement 1, (pp. 41-46), 2008, 6 pages.
International Preliminary Report on Patentability for International Application No. PCT/EP2018/054470, dated Oct. 18, 2019, 15 pages.
International Search Report and Written Opinion for International Application No. PCT/EP2018/054470, dated Apr. 24, 2018, 12 pages.
Malkowicz, "The role of diethylstilbestrol in the treatment of prostate cancer," Urology 58, Supplement 2A, (pp. 108-113), Aug. 2001, 6 pages.
Phillips et al., "Androgen Deprivation Therapy and the Re-emergence of Parenteral Estrogen in Prostate Cancer," Oncology and Hematology Review, vol. 10, No. 1, (pp. 42-47) 2014, 6 pages.
Shore et al., "New considerations for ADT in advanced prostate cancer and the emerging role of GnRH antagonists," Prostate Cancer and Prostatic Diseases 16, (pp. 7-15) 2013, 9 pages.

\* cited by examiner

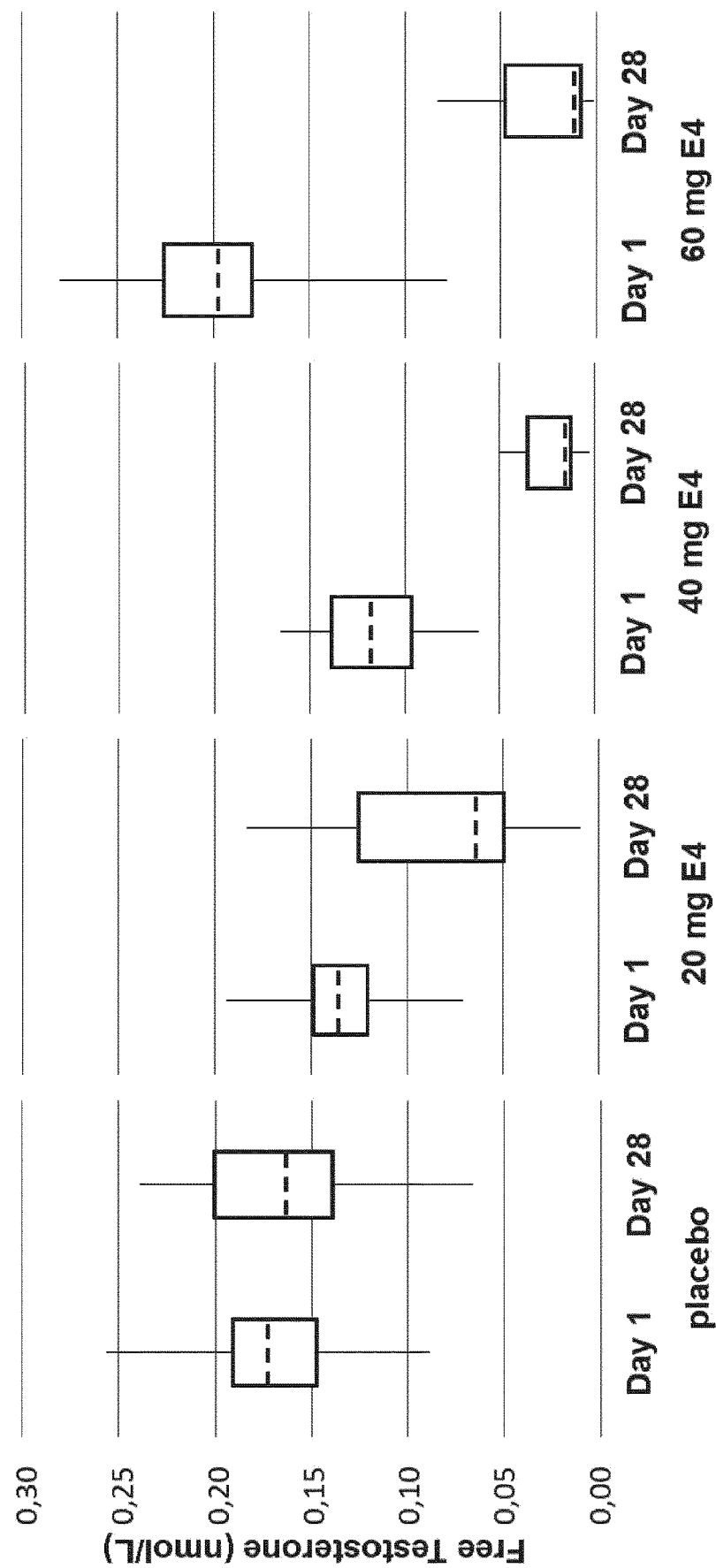

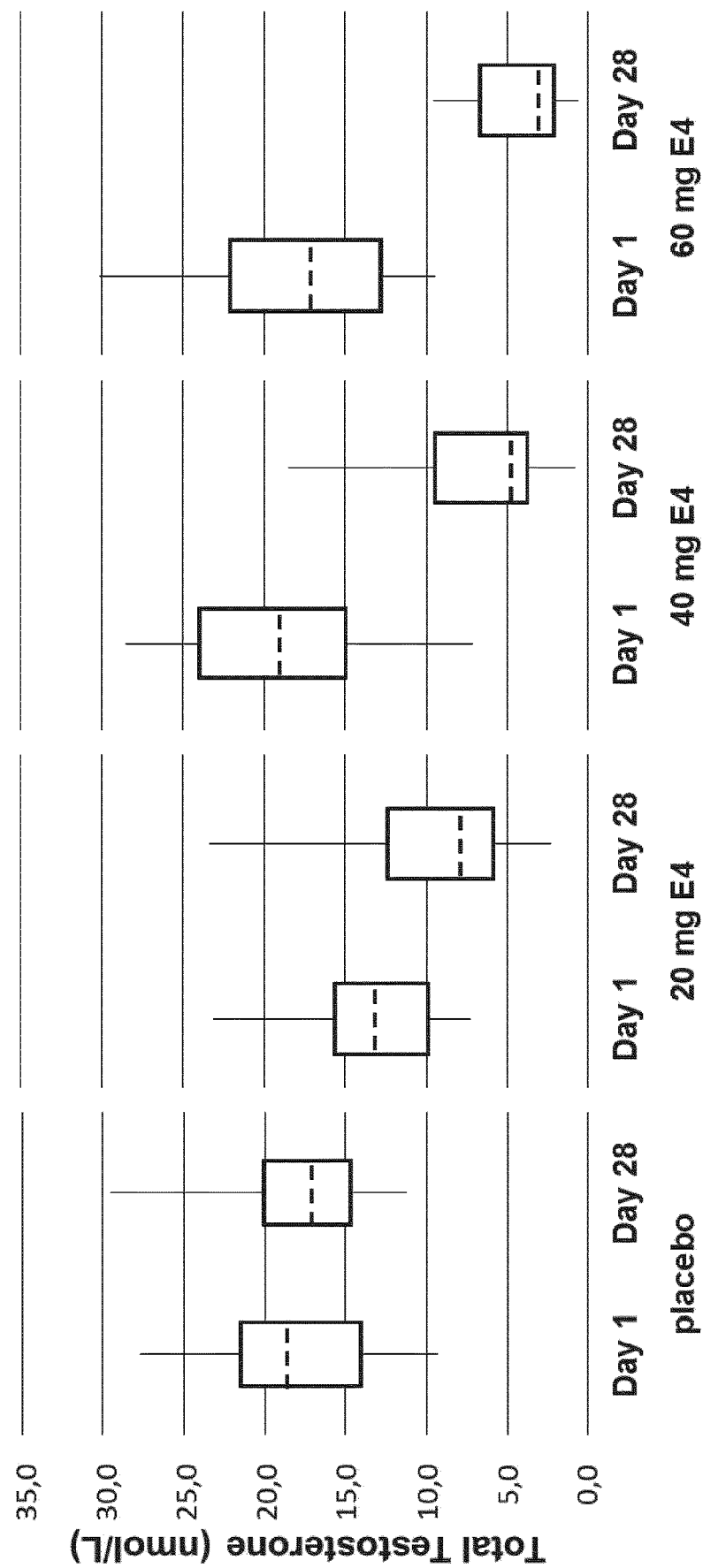

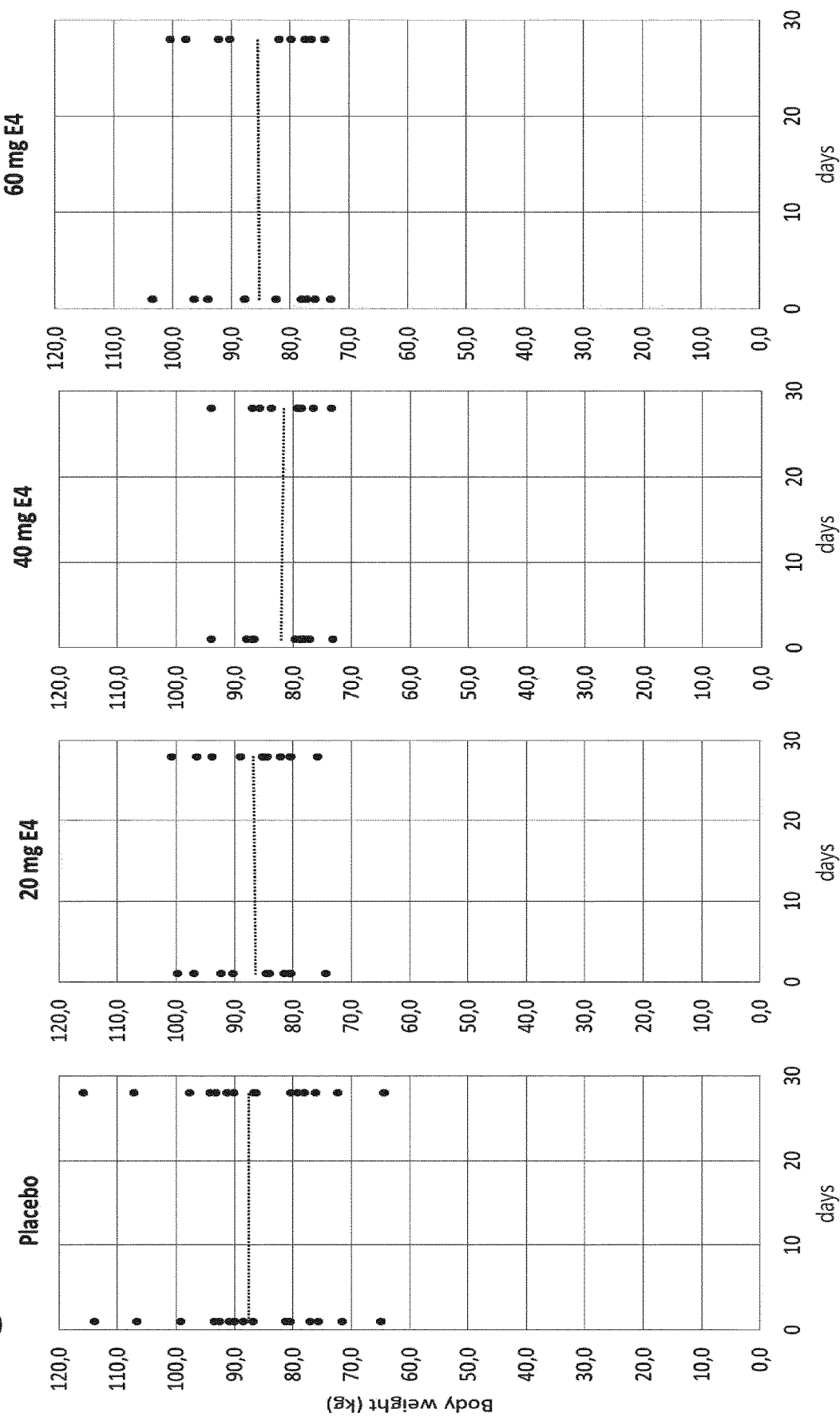

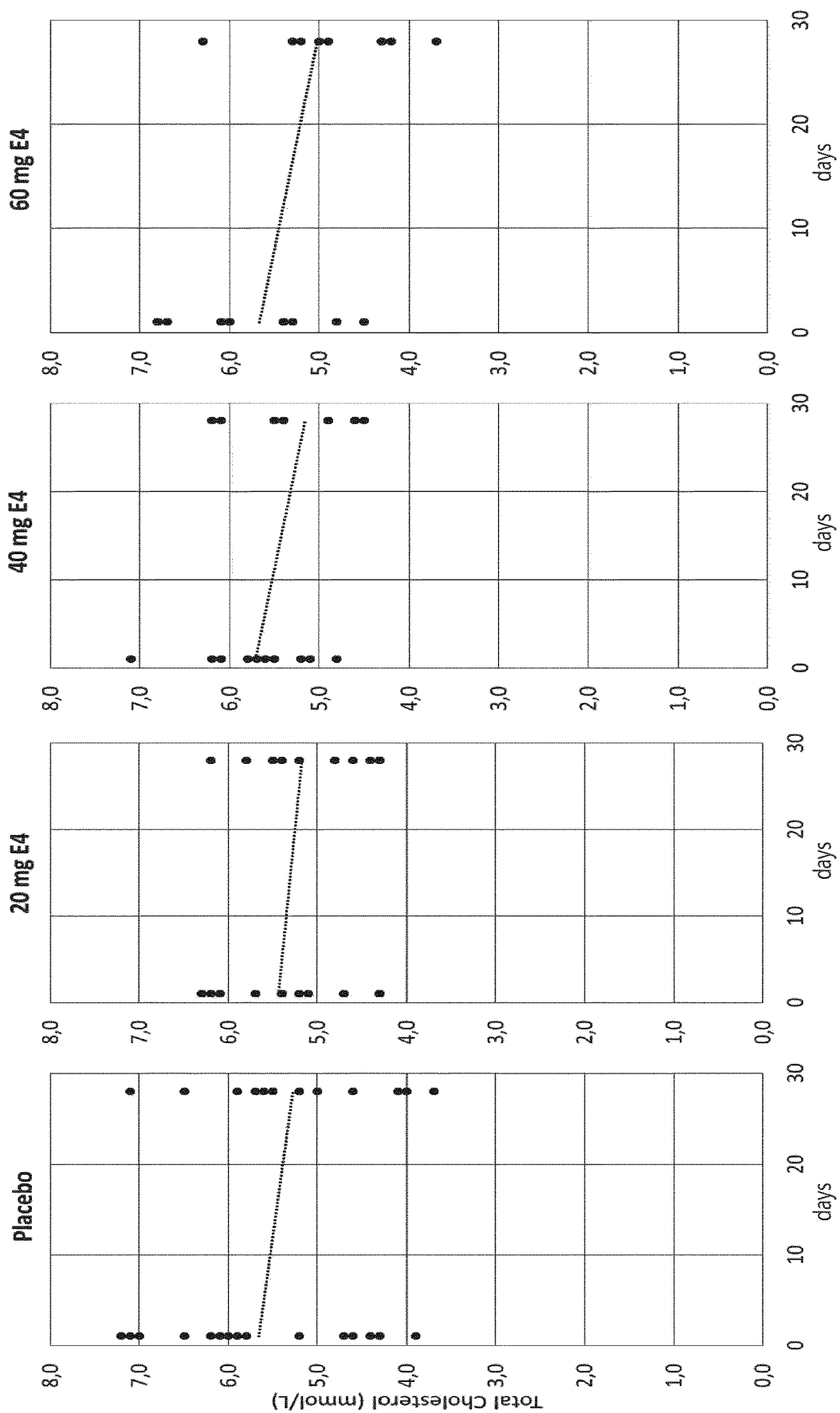

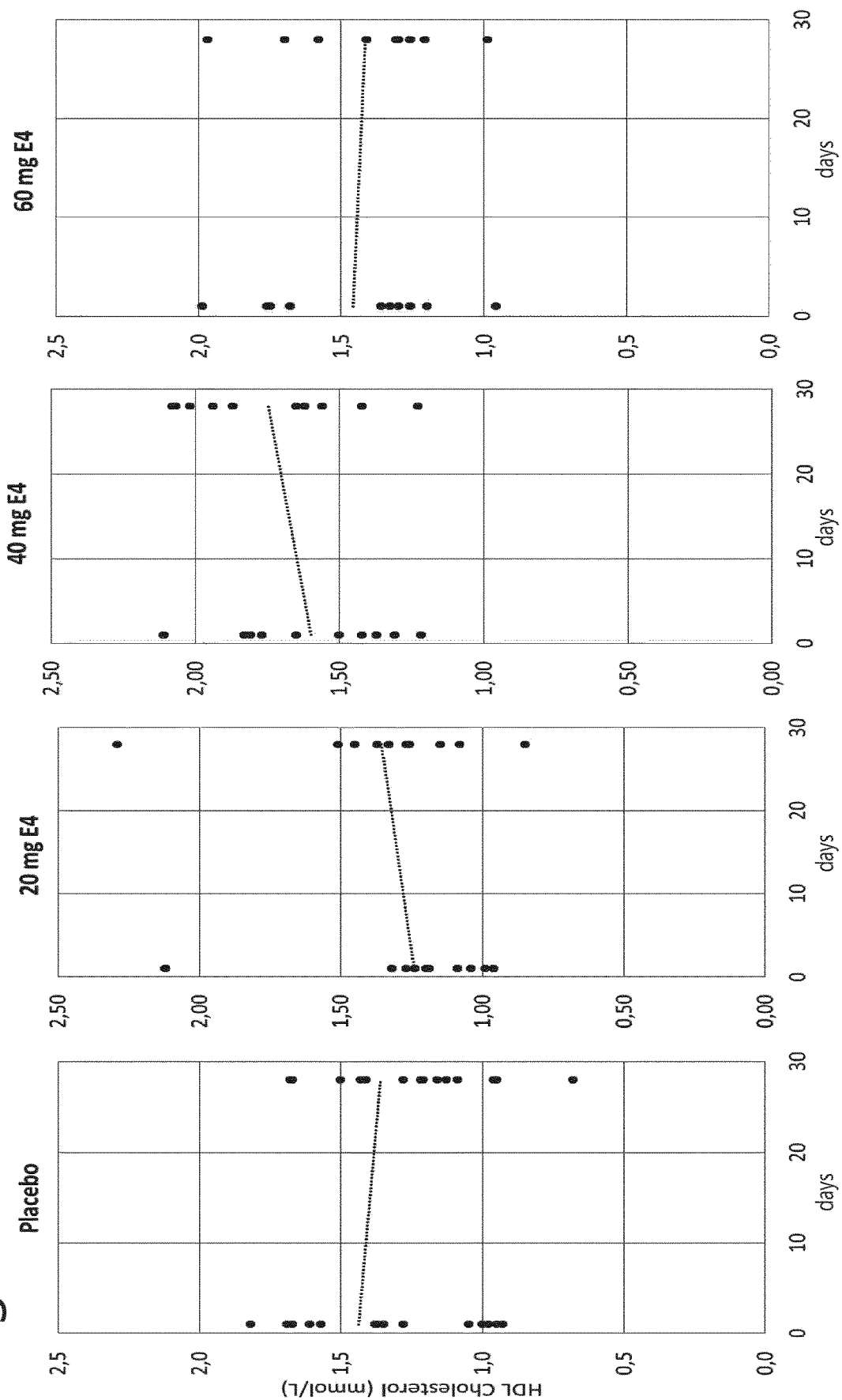

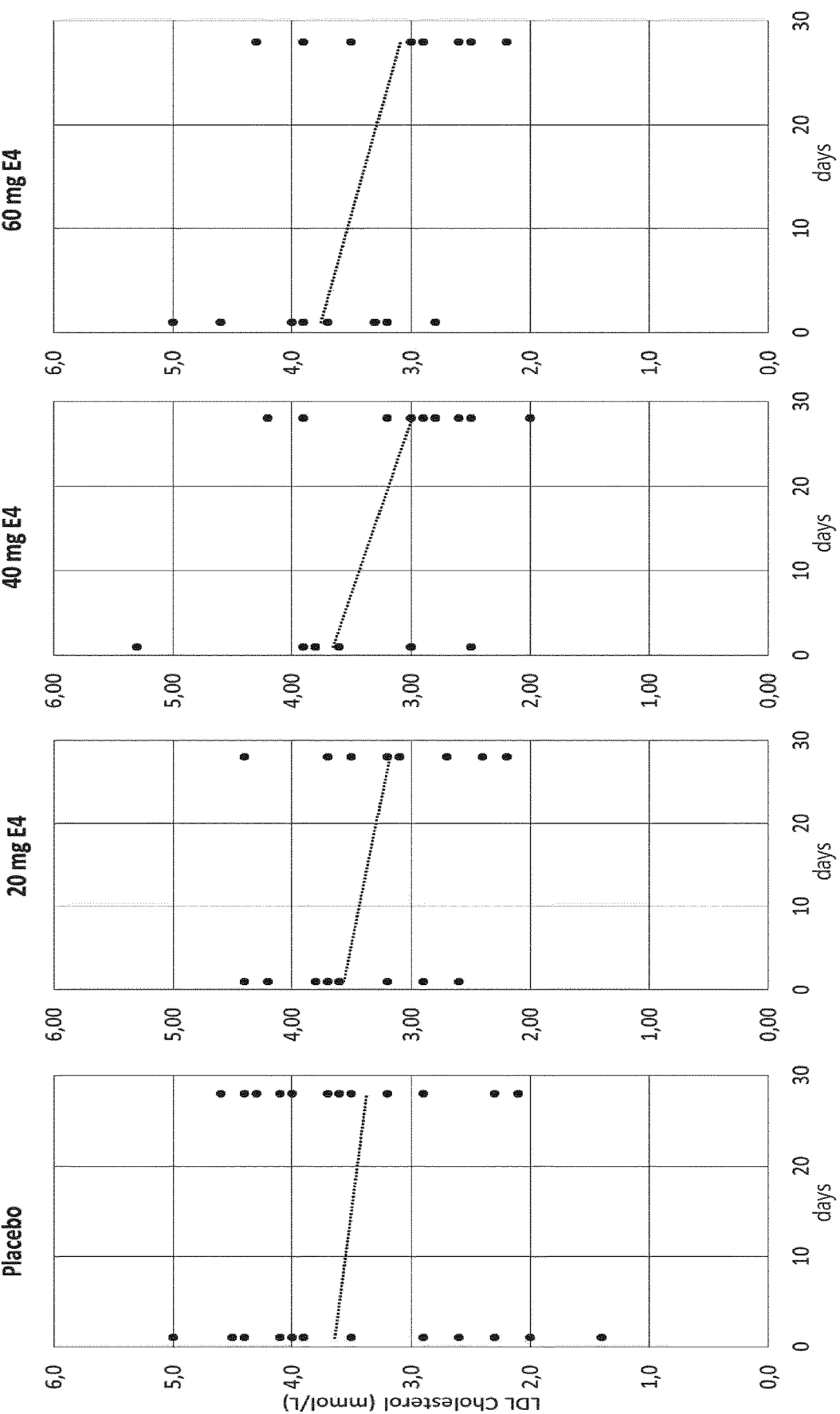

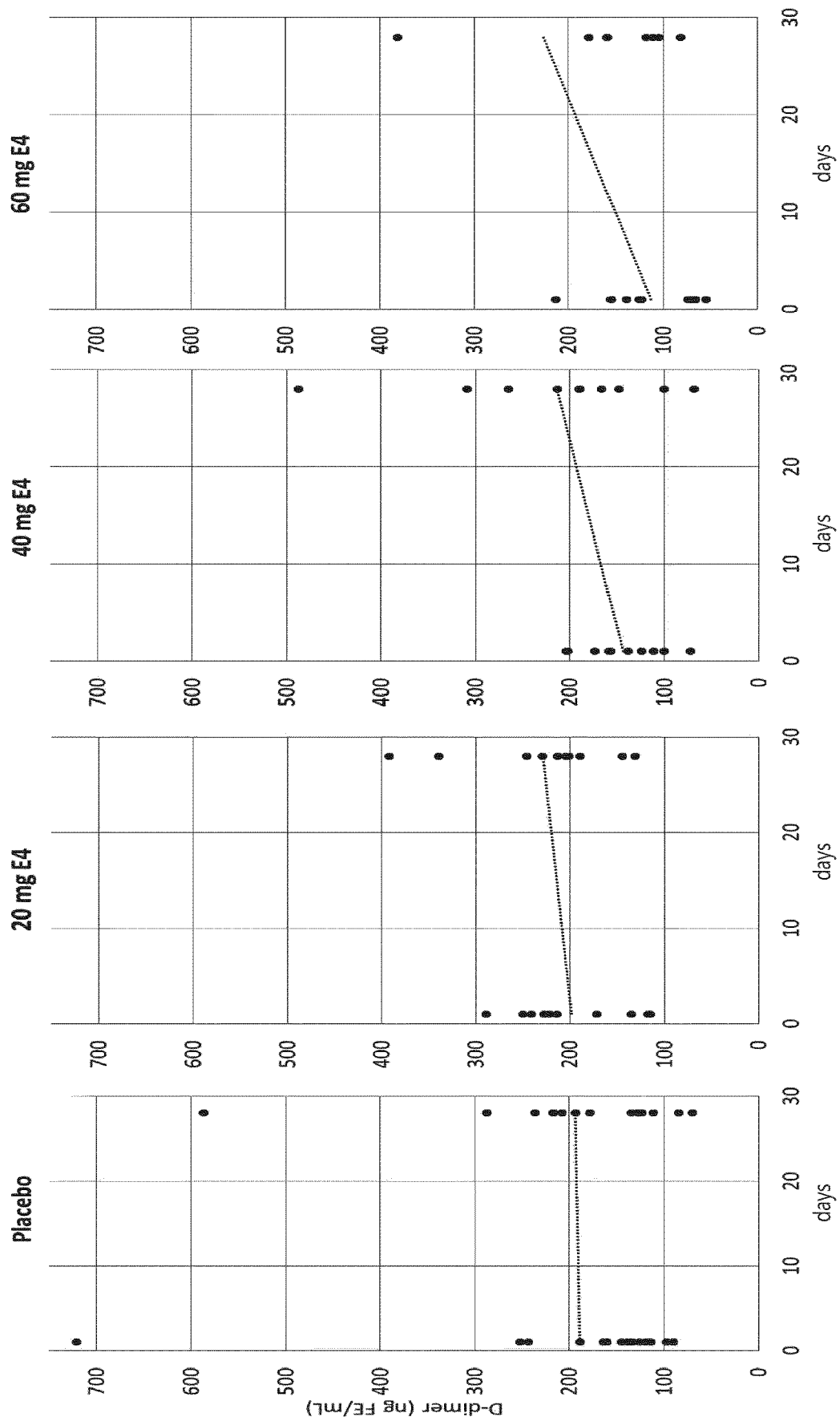

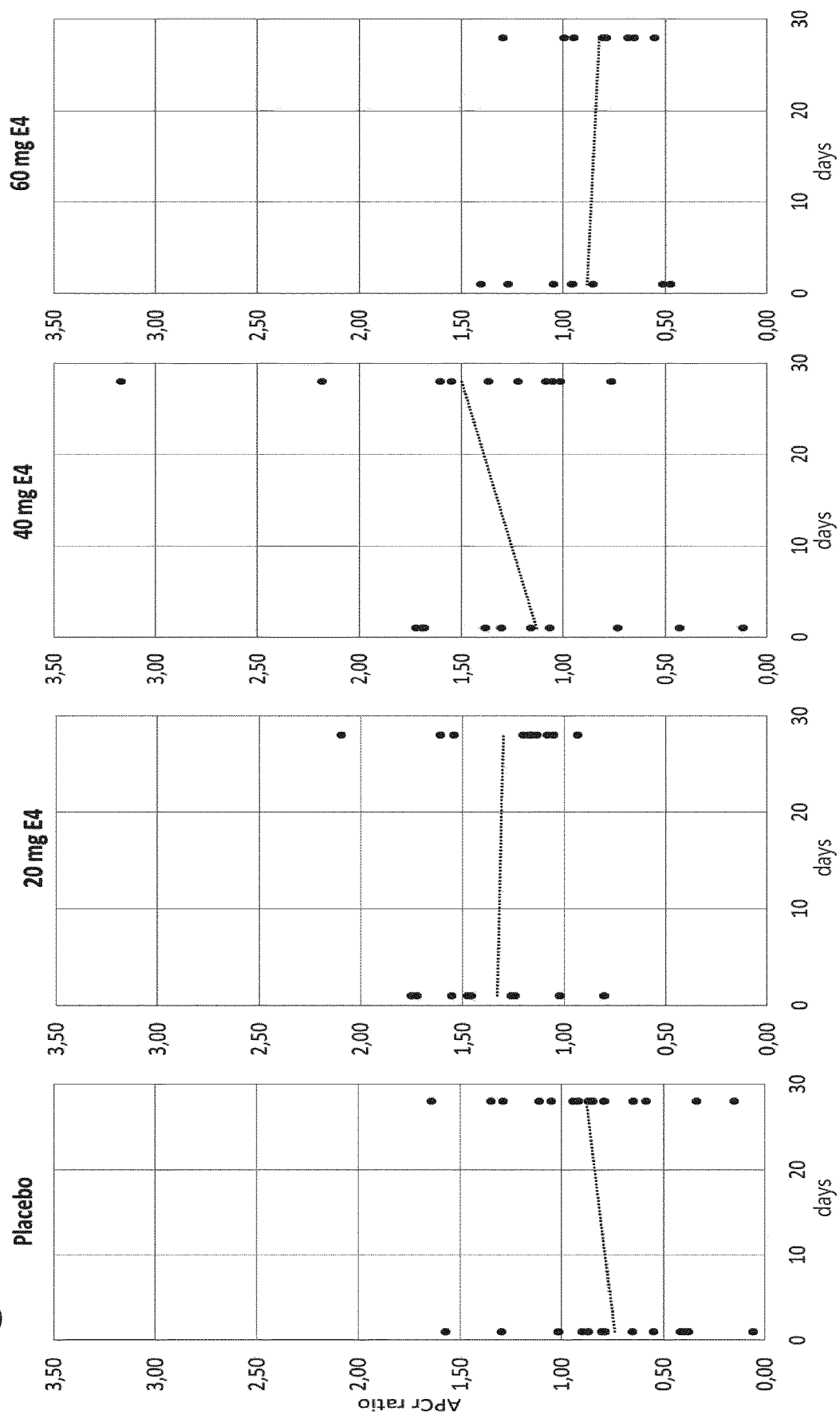

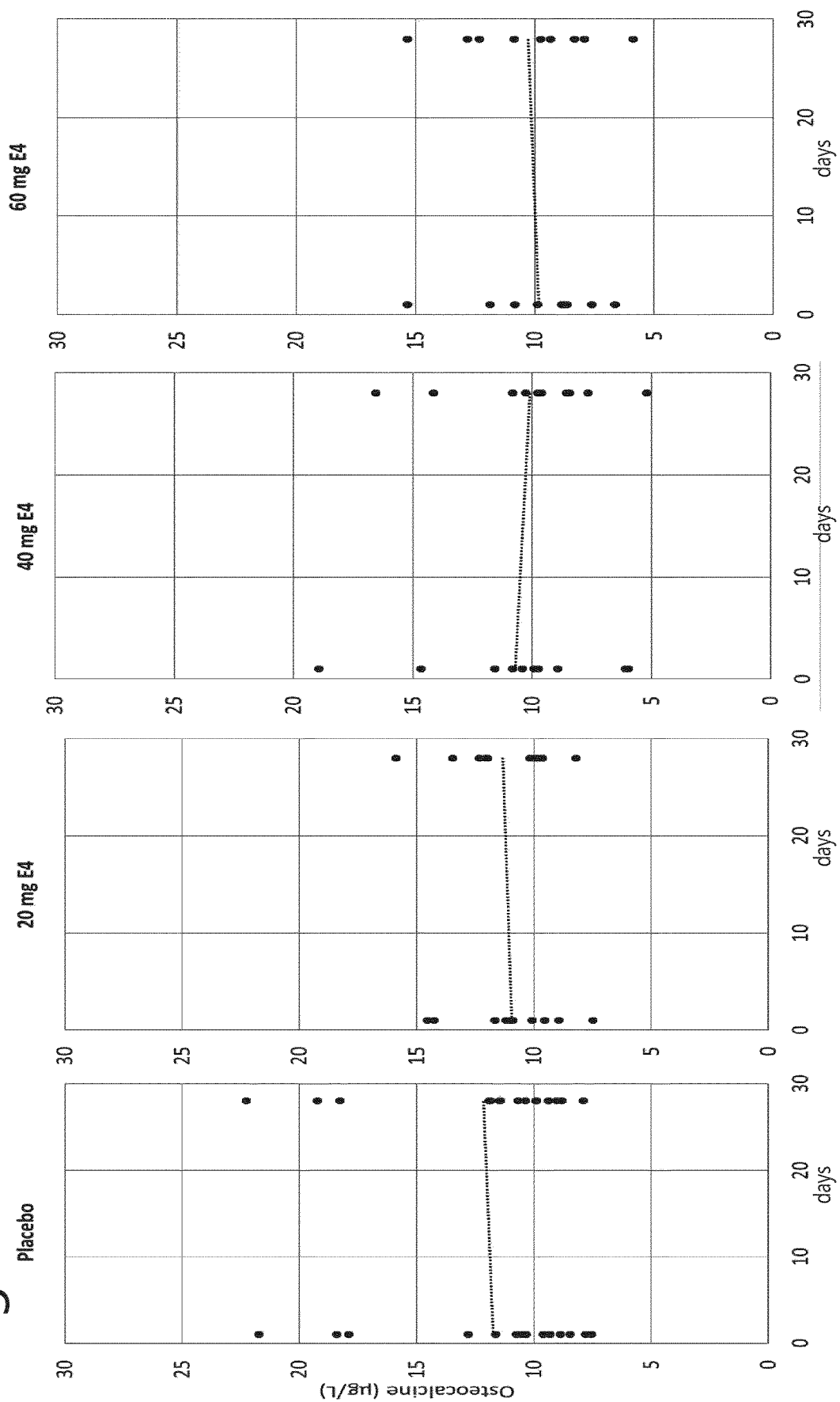

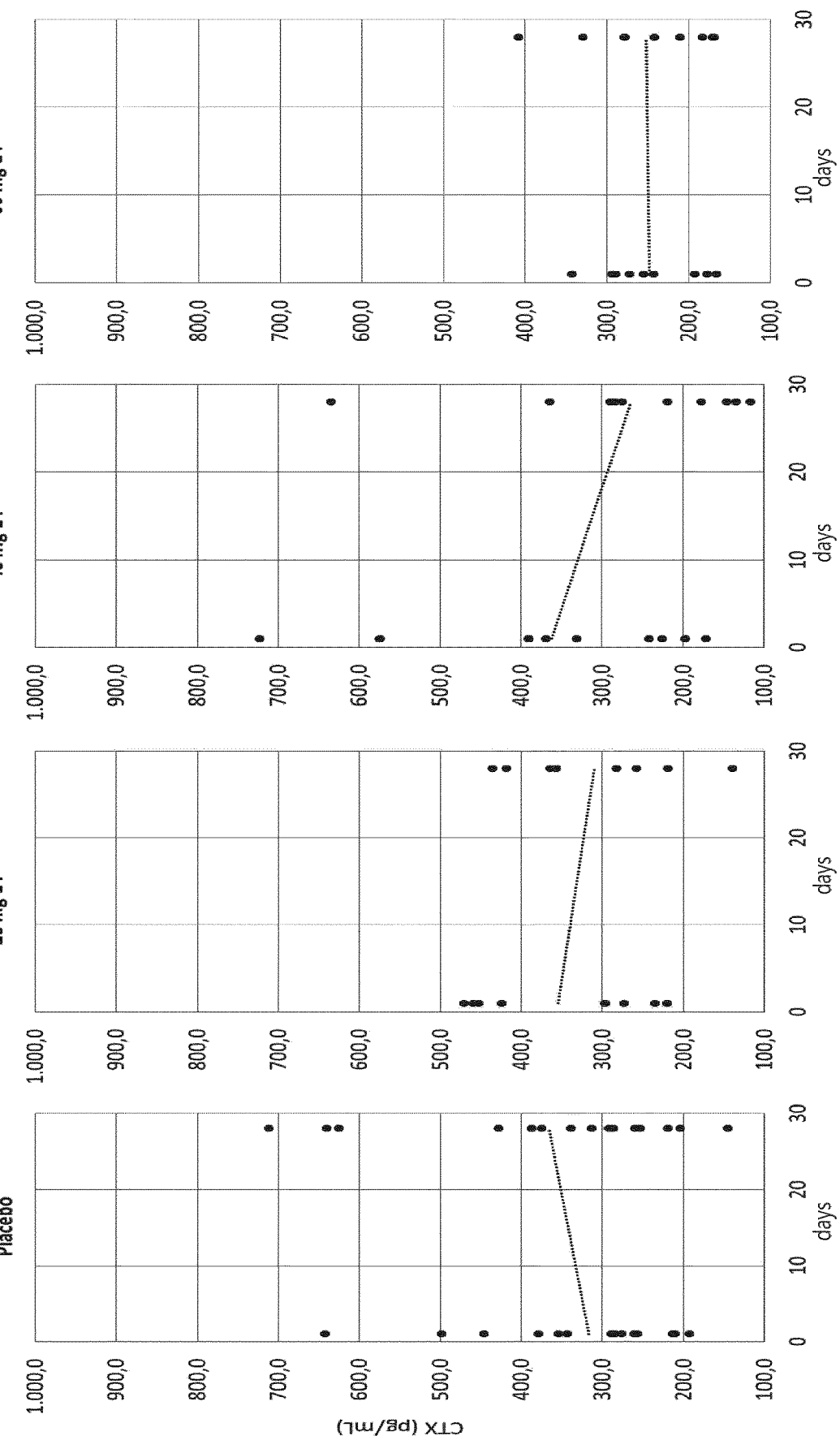

ADJUVANT THERAPY FOR USE IN PROSTATE CANCER TREATMENT

CROSS-REFERENCE TO RELATED APPLICATIONS

This application is a continuation of International Application No. PCT/EP2018/054470, filed Feb. 23, 2018, which claims the benefit of and priority to European Application No. 17184320.4, filed Aug. 1, 2017, both of which are hereby incorporated by reference herein in their entireties.

FIELD OF THE INVENTION

The present invention relates to the field of prostate cancer treatment, and in particular the field of prostate cancer treatment by Androgen Deprivation Therapy (ADT). The present treatment involves oral administration of an estetrol component in conjunction with ADT.

BACKGROUND ART

Prostate cancer is the second leading cause of cancer mortality in men in the USA. For the past six decades, hormonal therapy has been an important treatment of advanced prostate cancer. One such method employs diethylstilbestrol (DES) to suppress endogenous androgen production. DES is a substance that is known to exhibit estrogenic activity. However, the use of DES is marred by significant cardiovascular toxicity. Strategies to reduce thromboembolic events, such as dose reduction or the use of warfarin sodium were less than satisfactory (Malkwicz et al., "The role of diethylstilbestrol in the treatment of prostate cancer", Urology 2001 August; 58(2 Suppl 1): 108-13). In addition, the application of DES is believed to enhance the risk of breast cancer in men.

Nowadays, the use of DES and other estrogens has been replaced by treatments with Gonadotropin hormone Releasing Hormone (GnRH) agonists (at present the first choice treatment), antagonists and also anti-androgens treatments (such as enzalutamide, marketed as Xtandi®), which became available more recently.

When the treatment with GnRH agonists is started, during the first 2-3 weeks Luteinizing Hormone (LH) and Testosterone (T) levels are increased considerably which is a very undesirable side effect and may cause exacerbation of symptoms, especially pain caused by bone metastases. Thereafter the GnRH receptor is down regulated and LH and T are inhibited.

Since Androgen Deprivation Therapy (ADT) induces low levels of estrogen (as estrogens in men results from the aromatization of androgens), which in turn induce hot flushes and sweatings, arthralgia, sleep disturbances, cognition problems and memory loss, unfavourable lipid changes, mood changes (depression/irritability), fatigue, changes in body composition and very importantly, bone loss (osteoporosis and osteopenia) and fractures, it has been proposed to supplement those patients treated with ADT with estrogens.

Oral estrogen administration, however, induces an increase in the risk for thromboembolic and cardiovascular events because of first pass hepatic metabolism. For this reason, it is not considered a viable option.

Some authors have proposed to use transdermal estrogen instead (Phillips et al, *Oncology and Hematology Review*, 2014; 10(1):42-47). This can be delivered in the form of patches or gels to be applied daily. Patient compliance with these routes of administration is however a problem since these modes of administration represent a significant daily burden.

Other avenues to administer estrogens in the context of prostate cancer treatment by Androgen Deprivation have been proposed, such as in WO2004/096259. This application teaches to administer, in parallel to a sustained release formulation of a "GnRH, agonists of GnRH or antagonists of GnRH", a second sustained release formulation comprising an estrogenic composition in order to reduce the enhanced loss of bone mineral density or the hot flushes that are normally caused by the administration of a GnRH composition.

As specified by the applicants of WO2004/096259, however, the release of the estrogenic component has to be limited, during the second phase of the release, to a rate between about 10 and 100 µg of estradiol equivalent per day, preferably not exceeding about 50 µg of estradiol equivalent per day. This is because, due to the increased cardiovascular risks induced by the administration of estrogens, the applicants of WO2004/096259 have to solve the dilemma of administering enough estrogens to effectively counteract the negative side effects of GnRH administration without unnecessarily increasing the risk associated with high levels of estrogens (WO2004/096259 at page 10, line 21 to page 11, line 4). They propose to that extent a sustained release formulation which permits to achieve a serum estradiol equivalent level of from about 10 pg/mL to about 50 pg/mL. It is worth noting here that estradiol binds to SHBG with high affinity of about 40% (Hammond GL at al., *Climacteric*. 2008; 11 Suppl 1:41-6), such that only 60% of the amount delivered by the formulation of WO2004/096259 is bioavailable.

Dutman et al. (*The effects of the human fetal estrogen estetrol (E4) in healthy men to estimate its potential use for the treatment of prostate cancer*, Eur Urol Suppl (2017), 16(3) describes a single-centre, double-blind, randomised, placebo controlled, multiple dose study that was conducted in healthy men (40-70 years). A first cohort received daily a single dose of 20 mg estetrol and a second cohort 40 mg. It was found that total testosterone, free testosterone, FSH and estradiol levels decreased, LH levels did not change and SHBG levels increased. The changes observed suggest dose-dependency. Body weight and safety parameters did not change. During treatment with estetrol libido decreased in 8 of 20 men and nipple tenderness was reported by 7 of 20 men.

SUMMARY OF THE INVENTION

The present invention provides an adjuvant therapy for use in prostate cancer treatment by ADT that further decreases total and free testosterone levels, achieves effective estrogen supplementation and mitigates the negative side effects of ADT.

More particularly, the invention relates to a treatment of prostate cancer that comprises simultaneous oral administration, alongside the ADT, of an estetrol component in a high daily dose of at least 20 mg for at least 4 weeks, said estetrol component being selected from estetrol; esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. The present invention revolves around a number of surprising findings by the applicant.

Firstly, co-administration of the estetrol component in a high daily oral dose of at least 20 mg during a period of at least 4 weeks results in a pronounced additional decrease of T levels, especially of biologically active free T levels.

Secondly, co-administration of the estetrol component according to the invention effectively mitigates hypoestrogenic symptoms which are induced in prostate cancer patients by ADT.

Thirdly, co-administration of the estetrol component as described herein decreases the risk of arterial cardiovascular disease. This is further explained below in the context of the "improved lipid profile" which is observed in prostate cancer patients that have been treated in accordance with the present invention.

In case the ADT employs a GnRH agonist, combining the start of GnRH agonist administration with oral administration of the estetrol component offers the advantage that LH synthesis is inhibited immediately, thereby suppressing the initial increase of LH and T levels (the flare). This flare delays castration and causes exacerbation of the symptoms.

BRIEF DESCRIPTION OF THE FIGURES

FIGS. 1A-1E illustrate key sex hormone parameters measured during the clinical study described in Example 1. In particular, FIG. 1A relates to Free Testosterone, FIG. 1B to Total Testosterone, FIG. 1C to Sex Hormone-Binding Globulin (SHBG), FIG. 1D to Luteinizing Hormone (LH), and FIG. 1E to Follicle Stimulating Hormone (FSH). For all FIGS. 1A to 1E, the values measured at Day 1 and at Day 28 are shown for the placebo, estetrol 20 mg, estetrol 40 mg and estetrol 60 mg groups.

FIGS. 2A-2J illustrate key lipid, haemostasis and bone parameters measured during the clinical study described in Example 1. In particular, FIG. 2A relates to Body weight, FIG. 2B to Total Cholesterol, FIG. 2C to HDL Cholesterol, FIG. 2D to LDL Cholesterol, FIG. 2E to Triglycerides (TG), FIG. 2F to D-Dimer, FIG. 2G to Fragment 1+2, FIG. 2H to APCr ratio, FIG. 2I to osteocalcin and FIG. 2J to C-telopeptide (CTX-1). For all FIGS. 2A to 2J, the values measured at Day 1 and at Day 28 are shown for the placebo, estetrol 20 mg, estetrol 40 mg and estetrol 60 mg groups.

DETAILED DESCRIPTION OF THE INVENTION

Figure 1C:
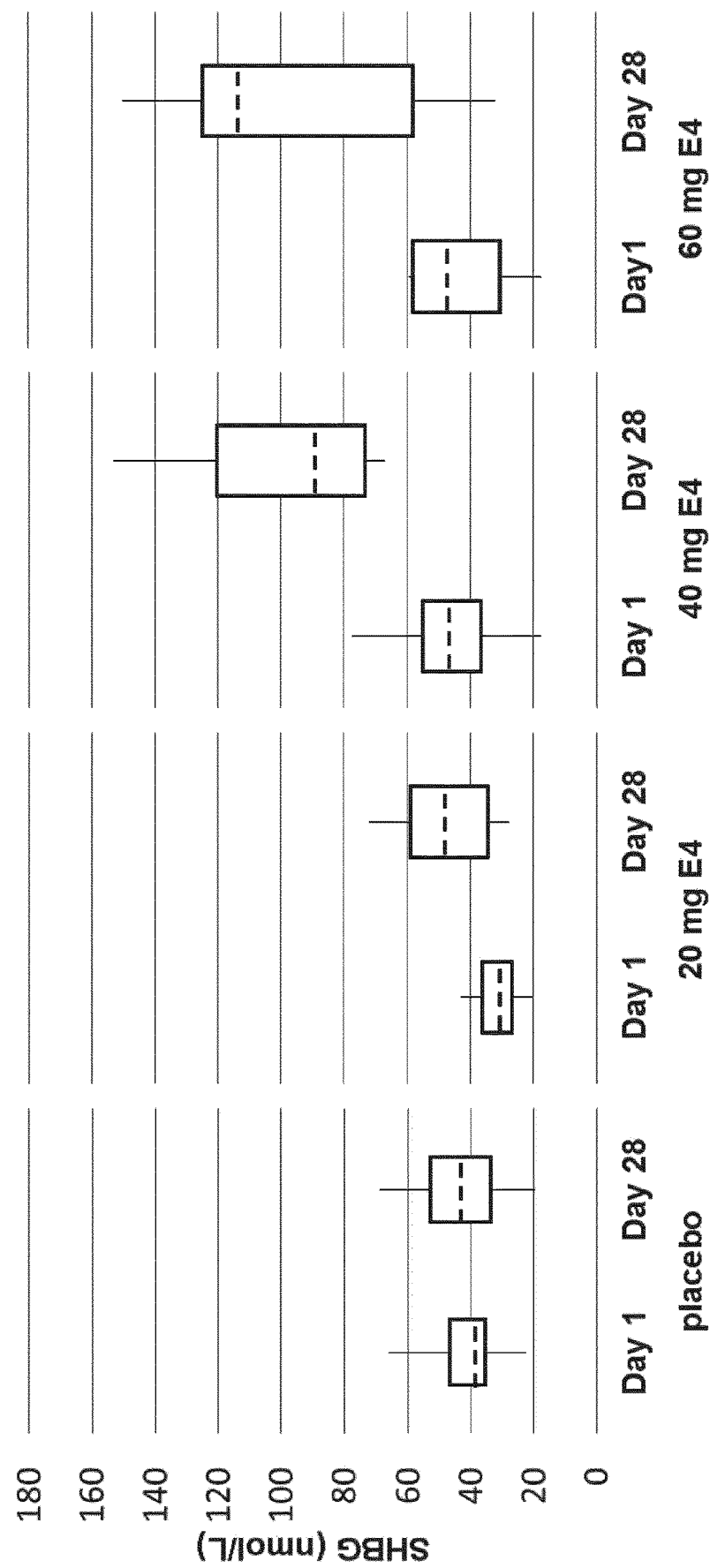

A first aspect of the present invention relates to the treatment of prostate cancer in a patient, said treatment comprising androgen deprivation therapy and co-administration of the estetrol component (adjuvant therapy) in a daily dose of at least 20 mg for at least 4 weeks, said estetrol component being selected from estetrol; esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof.

Definitions:

The term "estetrol component", as used throughout this document, refers to substances selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. Even more preferably, the estetrol component is estetrol (including estetrol hydrates). Most preferably, the estetrol component contained in the dosage unit is estetrol monohydrate.

The term "dose" or "dosage", as used herein, unless indicated otherwise, refers to an administered amount of estetrol component that is equivalent to the specified oral dose of estetrol monohydrate. Thus, for example, a daily oral dose of 40 mg of a particular estetrol component is a dose of that estetrol component that is equivalent to a daily oral dose of 40 mg of estetrol monohydrate.

Methods of Treatment

In the present treatment, the estetrol component is preferably administered to a prostate cancer patient undergoing ADT, in a dosage of not more than 80 mg per day, more preferably of not more than 60 mg per day.

The estetrol component is preferably co-administered alongside the ADT, for as long as the ADT is applied.

In a preferred embodiment, the estetrol component is administered for a period of 12 weeks, most preferably for at least 50 weeks.

In a particular preferred embodiment, the estetrol component is co-administered once daily in a convenient once-daily unit dose.

In the present treatment, the estetrol component is preferably administered in an amount sufficient to achieve an estetrol plasma trough concentration of at least 600 pg/mL, preferably of at least 1000 pg/mL, more preferably at least 1500 pg/mL, still more preferably at least 2000 pg/mL.

Generally the resulting estetrol plasma trough levels will not exceed 20 000 pg/mL, preferably it will not exceed 18 000 pg/mL, more preferably it will not exceed 16 000 pg/mL, still more preferably it will not exceed 14 000 pg/mL. As used herein, "trough levels" means the lowest concentration that a drug reaches before the next dose is administered.

The safety of the estetrol component is a key aspect of the present treatment as it enables much more effective estrogen supplementation than can be achieved using other estrogens. Furthermore, due to the pronounced testosterone lowering effect that is achieved by co-administration of the estetrol component, the present method is more effective than ADT per se.

The androgen deprivation therapy that is employed in accordance with the present treatment preferably comprises administration of an androgen inactivator selected from GnRH agonists, GnRH antagonists, anti-androgens and combinations thereof. More preferably, said ADT comprises administration of GnRH agonist.

As a consequence of the lowering effect of the estetrol component on T levels, the treatment of the invention allows, in specific embodiments, for a particular GnRH agonist, antagonist, or anti-androgen, to achieve a reduction of 5%, preferably 10%, even more preferably 20% of the dose of said GnRH agonist, antagonist, or anti-androgen, while maintaining the same castrate levels of T. This effect is illustrated in FIGS. 1A and 1B, and is further described in Example 1.

Co-administration of the estetrol component in accordance with the present invention offers the advantage that it mitigates the negative side effects of ADT, and especially the unfavourable impact on lipid profile. In another embodiment, the treatment of the invention has a favourable effect on the lipid profile of the patient, as further defined herein below under "improved lipid profile".

The present treatment offers the advantage that it decreases the plasma total and/or free testosterone level in the patient more effectively than ADT without co-administration of the estetrol component.

The present treatment further offers the advantages that the LDL Cholesterol level in the patient is maintained at a lower level than without co-administration of the estetrol component, and without an unwanted increase in the TG levels as normally seen with estrogens. This effect is referred to herein as an "improved lipid profile".

Alongside the positive impact on LDL Cholesterol, the co-administration of the estetrol component contributes to the maintenance of a higher HDL Cholesterol level, as is demonstrated in Example 1 below. These three concurrent effects (decrease of LDL Cholesterol, increase of HDL Cholesterol and stable TG levels) are associated with a decreased risk of arterial cardiovascular disease. As used herein, "arterial cardiovascular disease" includes conditions such as arterial atherosclerosis and arterial thrombosis. "Arterial cardiovascular disease" includes, without limitation, peripheral arterial disease.

The co-administration of the estetrol component in the present treatment effectively prevents the loss of bone mass, as measured by bone mineral density, in the patient during the course of the combined treatment according to the invention—loss of bone mass which is normally observed in the patient during the course of treatment with ADT alone. In other words, while treatment with ADT alone causes a decrease in bone mass, the combined treatment according to the invention allows a prevention in loss of bone mass to be observed.

Furthermore, the co-administration of the estetrol component decrease the median daily hot flush score for the patient during the course of the combined treatment according to the invention by at least 40%, at least 60%, at least 80%, compared to the median daily hot flush score for the patient during the course of treatment with ADT alone. As used herein, the terms "median daily hot flush score" corresponds to the number of hot flushes multiplied by the average severity per day measured over a 7 days' time period. More details on the determination of this score can be found in the publication by Irani et al. from 2010 (*Lancet Oncol.* 2010, 11, 147-54).

In an embodiment where the ADT treatment comprises administration of a GnRH agonist, co-administration of the estetrol component according to the invention results in a faster PSA response in the patient in comparison to treatment with GnRH agonist alone, when the flare delays castration.

Compositions:

Another aspect of the invention relates to a pharmaceutical dosage unit adapted for oral administration, comprising as a first active ingredient from 20 to 80 mg of an estetrol component selected from estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms, and combinations thereof, and as a second active ingredient an androgen inactivator selected from GnRH agonists, GnRH antagonists, anti-androgens and combinations thereof.

Preferably, the estetrol component is estetrol (including estetrol hydrates). Most preferably, the estetrol component contained in the dosage unit is estetrol monohydrate.

The estetrol component of the invention is preferably contained in the dosage unit in an amount of not more than 60 mg.

The oral dosage unit according to the invention is preferably a solid or semi-solid dosage form such as tablets, capsules, cachets, pellets, pills, powders and granules. The term "solid or semi-solid dosage form" also encompasses capsules that contain a liquid, e.g. an oil, in which the present estetrol component is dissolved or dispersed. Tablets and equivalent solid and semi-solid dosage forms can suitably contain materials such as binders (e.g. hydroxypropylmethyl cellulose, polyvinyl pyrrolidine, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc).

Anti-androgens, such as enzalutamide (marketed as Xtandi®), may suitably be used in accordance with the present invention.

GnRH antagonists and agonists can also be used in accordance with the present invention. GnRH antagonists are preferred because agonist treatment initially stimulates both LH and FSH secretion, followed by profound suppression. The advantage of GnRH antagonists compared to GnRH agonists is that they cause immediate reduction of gonadotropin level, without initial increase of gonadotropin release (the flare). Thus, the undesirable effects of the GnRH agonist treatment on LH and FSH secretion are avoided with antagonist treatment.

Co-administration of the estetrol component and a GnRH agonist also suppresses the undesirable flare. As explained herein before, co-administration of the estetrol component at the start of GnRH agonist treatment immediately inhibits LH synthesis and thereby suppresses the flare.

A number of such GnRH antagonists are available, such as cetrorelix, ganirelix, abarelix, or degarelix. The corresponding commercially available formulations have the following approved doses and routes of administration:

cetrorelix: 0.25 mg subcutaneous injection, once daily;

ganirelix: 0.25 mg subcutaneous injection, once daily;

abarelix: 100 mg every 4 weeks intramuscular;

degarelix: starting dose of 240 mg subcutaneous, then after 4 weeks maintenance dose of 80 mg every 4 weeks subcutaneous.

In a particular embodiment where the treatment involves the use of a GnRH antagonist, a dose of from 0.05 mg to 5 mg per day, preferably a dose of from 0.1 mg to 1 mg per day, is used.

In another particular embodiment where the treatment involves the use of an injectable long acting GnRH antagonist, a dose of from 10 mg to 500 mg, preferably a dose of from 50 mg to 250 mg, is used every week, every 2 weeks, every 4 weeks, every 2 months, every 3 months or every 6 months.

Oral GnRH antagonists are additionally known in the art, such as elagolix, a non-peptide, orally-active GnRH antagonist that is currently in phase III clinical trials. Elagolix doses are 150 mg daily (oral) and 200 mg twice daily (oral). Other non-peptide, orally-active GnRH antagonists that are also in development include relugolix (TAK-385), KLH-2109, and ASP-1707.

In addition, a number of GnRH agonists are available, such as buserelin, goserelin, leuprolide, nafarelin, or triptorelin. The corresponding commercially available formulations have the following approved doses and routes of administration:

buserelin: initial dose (subcutaneous) of 500 µg every 8 hours for 7 days. During maintenance subcutaneous administration route 200 µg/day or intranasal administration route 400 µg (200 µg into each nostril) three times per day;

goserelin: 3.6 mg subcutaneous every 4 weeks;

leuprolide: 7.5 mg intramuscular or subcutaneous every 4 weeks, 22.5 mg every 3 months, 30 mg every 4 months and 45 mg every 6 months;

nafarelin: nasal spray, 200-400 µg two times a day;

triptorelin: 3.75 mg intramuscular every 4 weeks, 11.25 mg every 3 months, and 22.5 mg every 6 months.

By using an oral GnRH antagonist or anti-androgen, the method of treatment of the invention may be applied using a purposely-developed oral formulation, such as a tablet, comprising a combination of the GnRH antagonist together with the estetrol component, e.g. both in a daily dosage amount.

In a particularly preferred embodiment of the invention, the dosage unit is a combined oral formulation which comprises a GnRH antagonist or an anti-androgen, together with the estetrol component.

Kit-of-Parts

Yet another aspect of the invention relates to a kit-of-parts comprising a first pharmaceutical composition comprising an androgen inactivator selected from GnRH agonists, GnRH antagonists, anti-androgens and combinations thereof; and a second pharmaceutical composition adapted for oral administration comprising 20 to 80 mg of an estetrol component selected from estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms, and combinations thereof, together with instructions for use according to the treatment of prostate cancer as described herein.

The present invention has been described above with reference to a number of exemplary embodiments. Modifications and alternative implementations of some parts or elements are possible, and are included in the scope of protection as defined in the appended claims.

EXAMPLES

Example 1: Safety, Pharmacokinetics and Pharmacodynamics of Estetrol in Healthy Men A phase I, double-blind, randomised, placebo-controlled, multiple dose study to evaluate the safety, pharmacokinetics and pharmacodynamics of multiple dosages of estetrol in healthy men.

Male participants aged between 40 and 70 years were allocated to one of the following groups:

Group 1: 20 mg E4 (estetrol) or placebo;
Group 2: 40 mg E4 (estetrol) or placebo;
Group 3: 60 mg E4 (estetrol) or placebo.

A total of 15 subjects were assigned to each dose group: 10 subjects were randomised to receive the active treatment (E4), 5 subjects were randomised to receive placebo treatment. In total 60 subjects participated in this study. Randomisation to one of the treatment groups took place after a participant was found to be eligible, at Visit 2.

Dosing began with Group 1. The other groups were dosed consecutively. Dose escalation to the next E4 dose group proceeded based on reported adverse events (AEs), SHBG levels, lipids and haemostatic parameters. The decision to continue with the next higher E4 dose level was made by the Investigator, an independent expert and the Sponsor.

E4 was supplied as tablets and taken orally every morning between 8:00-10:00 am, for 28 days. The total duration of the study, including screening was 84 days for each subject (Screening from Day −28 till Day −1, Clinical part from Day 1 till Day 56).

Methods of Evaluation

Primary Parameters:

There were two primary outcome parameters in this study. First primary parameter was the safety evaluation of E4. Safety variables included vital signs, routine laboratory tests, physical examination, ECG measurement and monitoring of (S)AEs.

Second primary parameter was the hormones related to prostate function. FSH, LH, E2, total testosterone, free testosterone and sex hormone-binding globulin (SHBG) were measured.

Secondary Parameters:

Secondary parameters included other pharmacodynamic and pharmacokinetic parameters. The pharmacodynamic parameters which were assessed are the following:

Haemostatic factors: (extrinsic) APC-resistance, prothrombin fragment 1+2, free tissue factor pathway inhibitor (TFPI), antithrombin activity, protein S activity, D-dimer, angiotensinogen;

Lipids and lipoproteins: total cholesterol, triglycerides, HDL-cholesterol, LDL-cholesterol and lipoprotein(a) (Lp(a));

Carbohydrates: fasting serum glucose;

Bone turnover markers: osteocalcin, type I collagen telopeptide (CTX-1) and parathyroid hormone (PTH);

Prostate-specific antigen (PSA).

Pharmacokinetics were evaluated by measuring E4 trough levels on Day 2, 7, 14 and 28. Furthermore, on Day 28 before and at several time points after dosing E4 concentrations were measured.

Results

A daily dose of 20 mg, 40 mg or 60 mg E4 was well tolerated by healthy men aged 40-70 years. No clinically relevant changes in vital signs, ECG, physical examination and body weight were observed.

FIGS. 1A-1E and 2A-2J display the marker levels at Day 1 and Day 28 for some hormones related to prostate function and for some lipid, haemostatic and bone parameters, respectively.

Figure 1D:
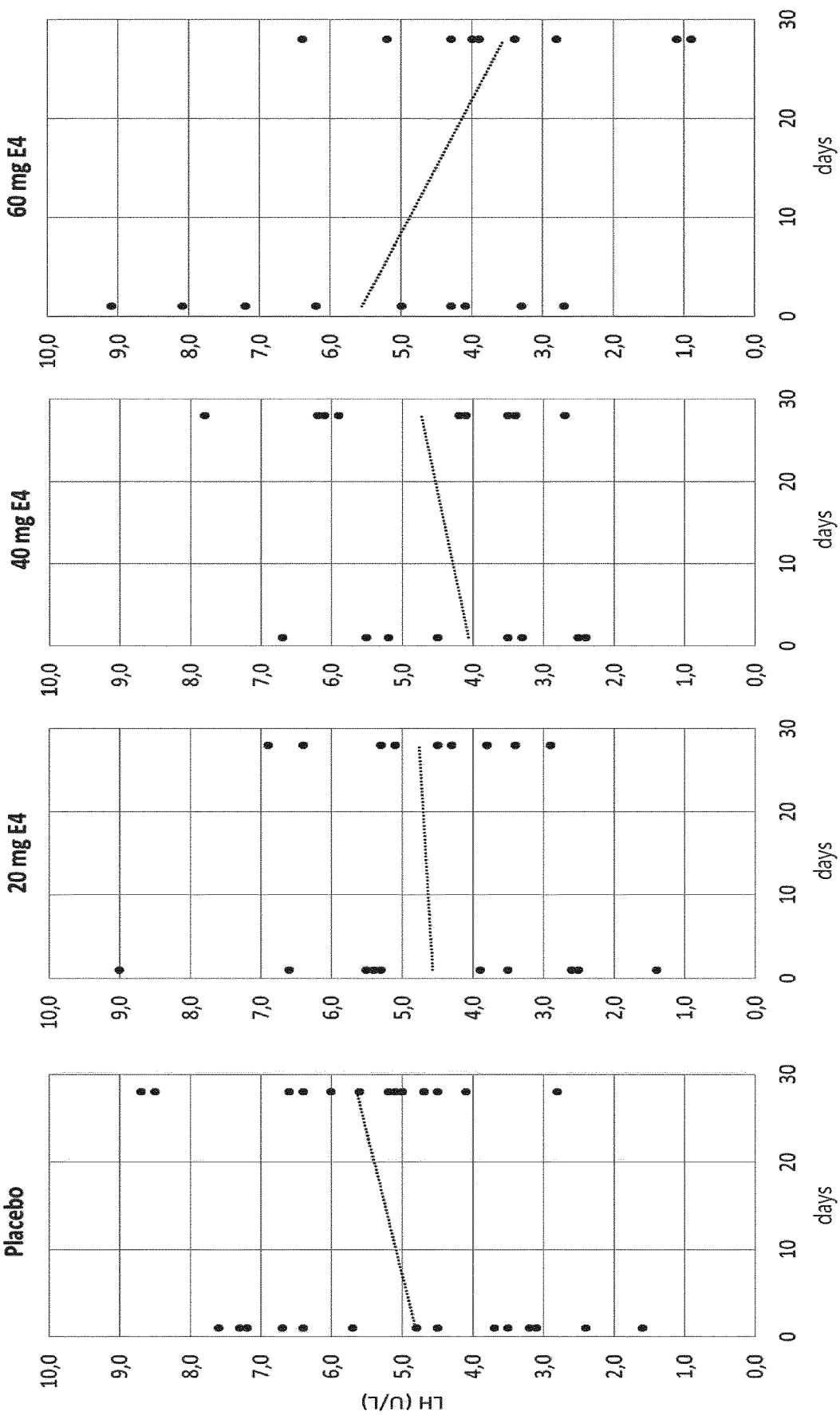
Figure 1E:
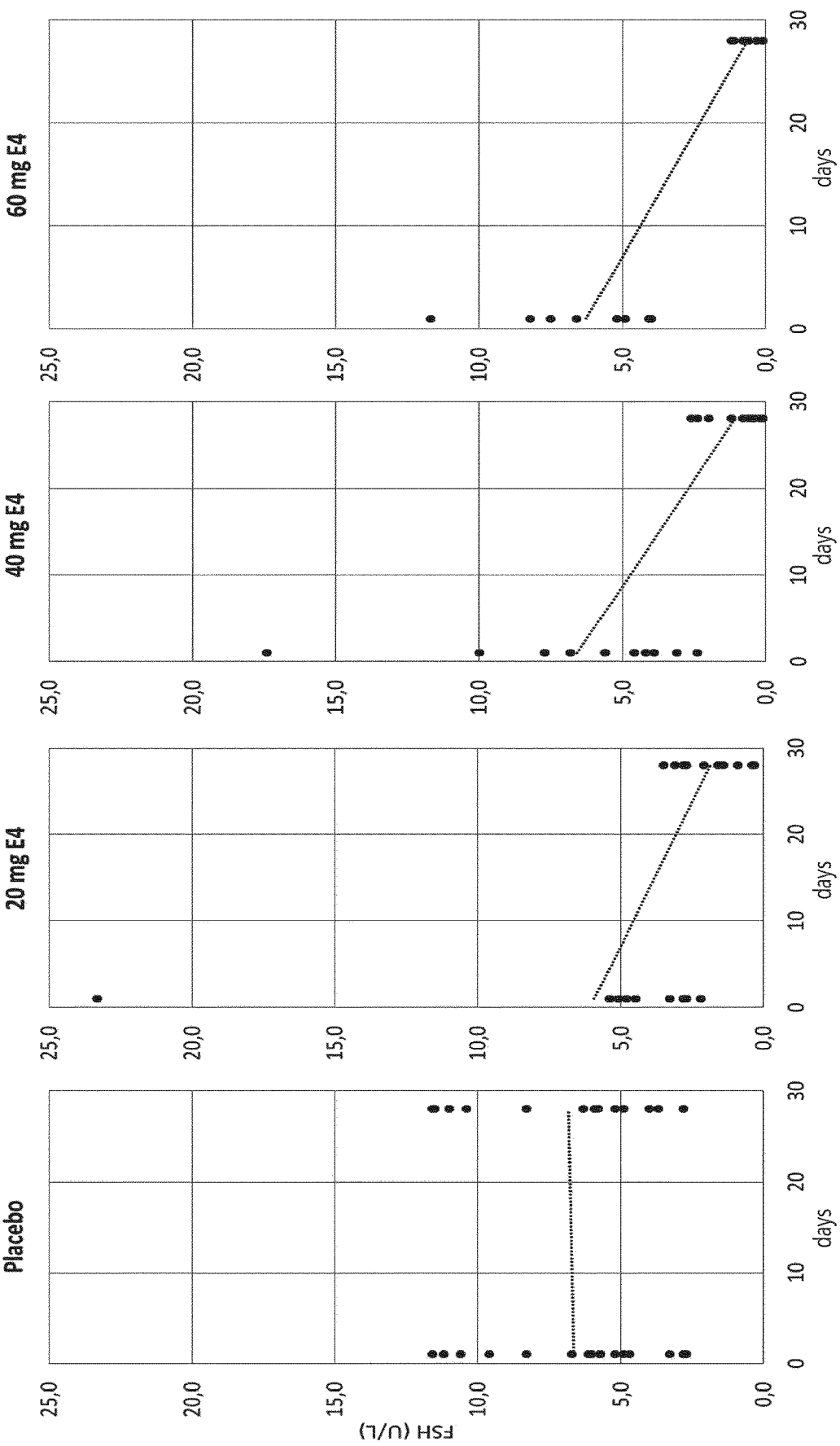
Figure 2E:
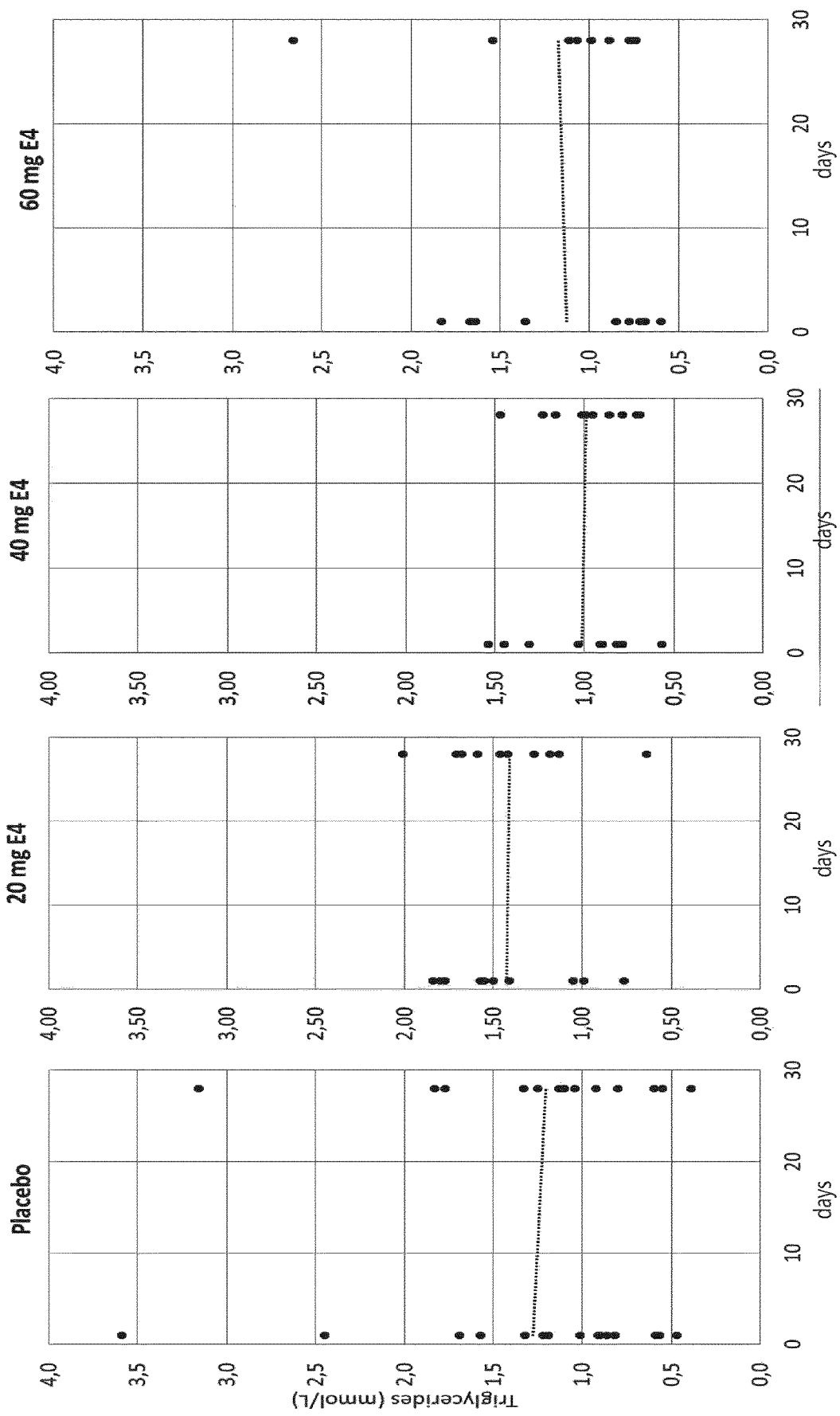
Figure 2G:
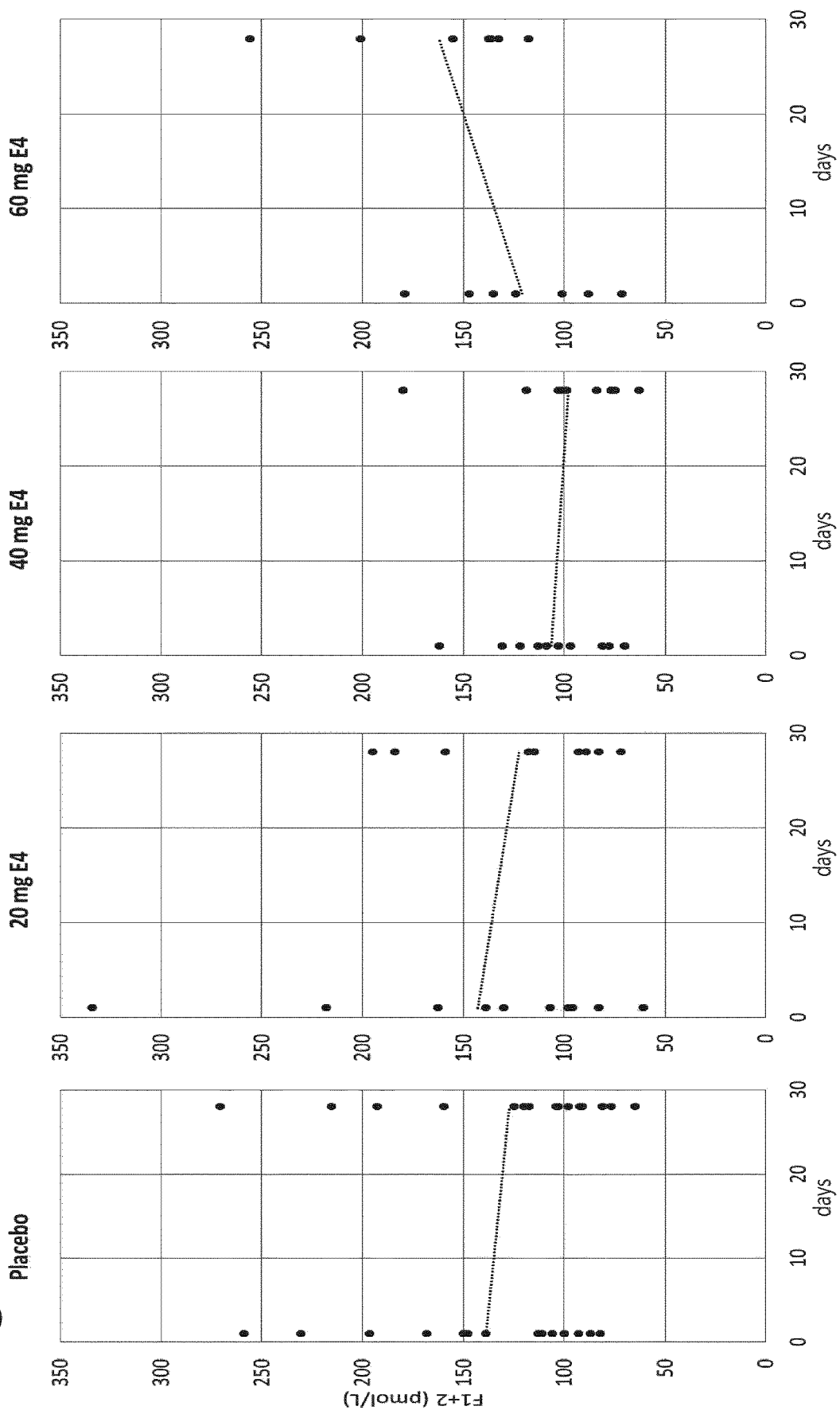

From FIGS. 1A and 1B it can be seen that the testosterone levels (free and total testosterone) were decreased by the treatments. In addition FIG. 1C shows the increase in SHBG induced by the treatments. The FSH levels (FIG. 1E) decreased, while not much change was observed for LH (FIG. 1D). The latter may be due to the time of sampling, since the LH levels decreased after E4 administration, but only for a few hours (this hormone is known to have a pulsatile secretion with a two hour interval in males).

The different parameters reported in FIGS. 2A-2J confirm the beneficial estrogenic effects of E4 on bone and the safety of the treatment at these doses. With respect to the lipids, a significantly lowering effect was observed on LDL Cholesterol of about 20%, accompanied with an small increase in HDL Cholesterol and no changes in TG.

Example 2: Estetrol Plasma Levels as a Function of Administered Dose

For each group dosed at 2, 10, 20, 40 and 60 mg estetrol daily (oral administration), 7 to 10 male patients were tested for their plasma content in estetrol at Day 7 and at Day 14.

For each dose group, the average trough level of all patients across both days was calculated.

As illustrated in Table 1, the results show a nice dose linearity.

TABLE 1

Trough plasma levels of estetrol as a function of the administered oral dose

| Daily estetrol oral dose, mg | Plasma level, pg/mL |
|---|---|
| 2 | 198 |
| 10 | 1056 |
| 20 | 2187 |
| 40 | 4417 |
| 60 | 6157 |

Example 3: Effect and Tolerability of Estetrol in Prostate Cancer Patients Treated with Androgen Deprivation Therapy Male patients who have histologically confirmed adenocarcinoma of the prostate and who are qualifying for treatment with androgen deprivation therapy (ADT: GnRH agonist) are included. The study is randomized placebo controlled.

Randomisation takes place after a patient is found to be eligible at the baseline visit. Subjects receive the study medication for a period of 24 weeks in total.

Subjects receive blinded study medication (oral administration) as follows:

Investigational product: GnRH agonist plus 40 mg estetrol (E4) per day;

Placebo: GnRH agonist plus placebo.

Medication should be taken in the morning between 8:00-10:00 AM. All patients concomitantly receive a prophylactic dose of dabigatran (220 mg once daily) or another anticoagulant.

A total of 30 patients is being dosed as follows: 20 patient in the estetrol group and 10 patients in the reference therapy group (placebo).

The primary objective is to assess the additional effects of E4 on total T and free T. Secondary objectives include the assessment of the effects of E4 on SHBG, PSA response and lipids and lipoproteins.

Other secondary objectives include the assessment of the effect of E4 on health related quality of life in prostate cancer patients being treated with ADT (using the European Organisation for Research and Treatment of Cancer Quality of Life Questionnaire EORTC QLQ-C30 (version 3.0) and the Expended Prostate Cancer Index Composite Short Form (EPIC 26)) and effects on hot flushes and bone turnover (bone markers and DEXA measurements).

It will be shown that the daily administration of estetrol at the prescribed dose is an effective therapy to improve efficacy and quality of life of ADT treatment for prostate cancer.

Example 4: Effects of Estetrol on Testosterone Suppression and Quality of Life in Prostate Cancer Patients Treated with Androgen Deprivation Therapy Male patients who have histologically confirmed adenocarcinoma of the prostate and who are qualifying for treatment with androgen deprivation therapy (ADT: GnRH agonist) participate in randomized placebo controlled study. Randomisation takes place after a patient is found to be eligible at the baseline visit. Subjects receive the study medication for a period of 24 weeks in total.

Subjects receive blinded study medication:

Investigational product: GnRH agonist plus 40 mg estetrol monohydrate (E4) p.o. per day;

Placebo: GnRH agonist plus placebo.

Selection of the GnRH agonist is left to the doctors treating the individual patients. Medication is taken in the morning between 8:00-10:00 AM.

A total of 60 patients is dosed as follows: 40 patient in the estetrol group and 20 patients in the reference therapy group (placebo).

Effects of medication on total T, free T, SHBG, hot flushes, PSA response, endocrine parameters, adrenal androgens and the lipid profile are assessed. Further assessed are the effects on health related quality of life (using the Functional Assessment of Cancer Therapy Prostate (FACT-P) questionnaire and a small questionnaire on the presence and absence of endocrine related symptoms (Q-man questionnaire)) and effects on bone turnover (bone markers).

It is found that daily oral administration of 40 mg estetrol improves efficacy of ADT, and improves quality of life of the prostate cancer patients.

What is claimed is:

1. A method of treating prostate cancer in a patient undergoing androgen deprivation therapy (ADT), comprising:
   (i) administering to the patient a GnRH agonist selected from the group consisting of buserelin, goserelin, leuprolide, nafarelin, and triptorelin, or a GnRH antagonist selected from the group consisting of cetrorelix, ganirelix, abarelix, degarelix, elagolix, relugolix, KLH-2109 (linzagolix), and ASP-1707 (opigolix), and
   (ii) orally co-administering estetrol in a daily dose of 20 mg to 60 mg for at least 4 weeks,
   wherein the co-administration causes a further decrease of free testosterone levels compared to administration of the GnRH agonist or the GnRH antagonist alone.

2. The method according to claim 1, wherein a GnRH agonist is administered.

3. The method according to claim 1, comprising orally administering a dosage unit comprising a GnRH antagonist and estetrol.

4. The method according to claim 1, wherein the estetrol is administered in a daily dose of no more than 60 mg.

5. The method according to claim 1, wherein the estetrol is co-administered once daily for at least 12 weeks.

* * * * *